United States Patent [19]
Pahlck et al.

[11] Patent Number: 5,888,483
[45] Date of Patent: Mar. 30, 1999

[54] NAIL BLEACH

[75] Inventors: Harold E. Pahlck, Waldwick; Leona Giat Fleissman, Ridgewood, both of N.J.; Anna Maria Vakirtzis, New Windsor, N.Y.

[73] Assignee: Avon Products, Inc., New York, N.Y.

[21] Appl. No.: 954,837

[22] Filed: Oct. 21, 1997

Related U.S. Application Data

[63] Continuation-in-part of Ser. No. 797,992, Feb. 12, 1997.
[51] Int. Cl.$^6$ .............................. A61K 6/00; A61K 7/00; A61K 7/04
[52] U.S. Cl. ............................................ 424/61; 424/401
[58] Field of Search ................................ 424/61, 62, 401

[56] References Cited

U.S. PATENT DOCUMENTS

| | | |
|---|---|---|
| 2,197,630 | 4/1940 | Carter . |
| 3,257,280 | 6/1966 | Richter . |
| 3,510,554 | 5/1970 | Balsiger . |
| 3,639,574 | 2/1972 | Schmolka . |
| 3,706,670 | 12/1972 | Gray .......................................... 252/95 |
| 3,887,702 | 6/1975 | Baldwin . |
| 3,954,974 | 5/1976 | Herzog et al. . |
| 4,104,333 | 8/1978 | Lee, Jr. et al. . |
| 4,260,701 | 4/1981 | Lee, Jr. . |
| 4,327,751 | 5/1982 | Evans .......................................... 132/7 |
| 4,344,932 | 8/1982 | Gordon . |
| 4,626,428 | 12/1986 | Weisberg et al. . |
| 4,631,186 | 12/1986 | Brown . |
| 4,696,757 | 9/1987 | Blank et al. . |
| 4,820,509 | 4/1989 | Yamazaki et al. . |
| 4,897,261 | 1/1990 | Yamazaki et al. . |
| 5,004,599 | 4/1991 | Scher . |
| 5,047,249 | 9/1991 | Rothman et al. . |
| 5,059,417 | 10/1991 | Williams et al. . |
| 5,066,484 | 11/1991 | Castrogiovanni et al. . |
| 5,139,570 | 8/1992 | Castrogiovanni et al. . |
| 5,217,710 | 6/1993 | Williams et al. . |
| 5,254,161 | 10/1993 | DeVido et al. . |
| 5,362,488 | 11/1994 | Sibley et al. . |
| 5,372,802 | 12/1994 | Barrows et al. . |
| 5,372,803 | 12/1994 | Williams et al. . |
| 5,449,403 | 9/1995 | Andrean et al. . |
| 5,456,902 | 10/1995 | Williams et al. . |
| 5,478,551 | 12/1995 | Busch, Jr. . |
| 5,484,586 | 1/1996 | Bedard . |
| 5,554,358 | 9/1996 | Williams et al. . |
| 5,607,664 | 3/1997 | Ascione et al. ............................ 424/59 |
| 5,622,691 | 4/1997 | Tricaud et al. ............................ 424/62 |

FOREIGN PATENT DOCUMENTS

| | | |
|---|---|---|
| 8-119836 | 5/1996 | Japan . |

OTHER PUBLICATIONS

*Modern Cosmeticology—The Principles and Practice of Modern Cosmetics* by Ralph G. Harry, Chemical Publishing Co., Inc., 1940, pp. 264–266 and title page.
*Cosmetic Safety—A Primer for Cosmetic Scientists*, by James H. Whittam, ed., pp. 272–277, 283, Marcel Dekker, Inc., 1987.
*The Chemical Formulary*, H. Bennett, ed., Chemical Publishing Co., Inc., 1951, pp. 90–91 & title page.
*Formulating with Hydrogen Peroxide*, Wetmur et al., Happi, pp. 52, 54, 56, Feb., 1997.
*Successful Use of Topical Vitamin E Solution in the Treatment of Nail Changes in Yellow Nail Syndrome*, Williams et al., Arch Dermatol—vol. 127, Jul. 1991, pp. 1023–1028.
*Fingernail Elongators and Accessory Nail Preparations*, p. 575, Belsam & Sagarin: Cosmetics Science Technology, 2d ed. 1972, vol. II.
Ullmann's Ency. of Industrial Chemistry, pp. 384, 392, vol. A8, *Detergents*, 1987.
Ullmann's Ency. of Industrial Chemistry, ed. 5, pp. 194, 197, *Peroxo Compounds, Inorganic*, vol. A19, 1991.
Kirk–Othmer Encyclopedia of Chemical Technology, ed. 3, V. 13, *Hydrogen Peroxide*, pp. 14–15, 30–31, 1981.
Kirk–Othmer Encyclopedia of Chemical Technology, ed. 3, V. 3, *Bleaching Agents*, pp. 944–945, 957, 1978.
Zimmerman's Complete Guide to Nonprescription Drugs, pp. 692–693, 1992.
*Bleaching* by Hans Ulrich Suss, pp. 191–199, Ullmann's Ency. of Industrial Chemistry, 1985.
Brochure entitled *Hydrogen Peroxide—Consumer Products*, by Solvay Interox, 12 pps. 1993.
Kirk–Othmer Encyclopedia of Chemical Technology, ed. 4, V. 13, *Hydrogen Peroxide*, pp. 964–966; 984–986; 989–990, 1992.
*Harry's Cosmeticology*, pp. 371, 373 and 374, 1982.
*Hydrogen Peroxide*, Merck Index, ed. II, 4725–4727, 1989.
Excerpt from Solvay Interox brochure entitled "Hydrogen Peroxide in Consumer Products", p. 2, copyright 1996.
Hydrogen Peroxide Technical Data Sheets, Ultra Cosmetic and PeroxClean Hydrogen Peroxide, 3 pages. 1996.
Material Safety Data Sheet, Ultra Cosmetic Hydrogen Peroxide, effective Mar. 8, 1996, 14 pps.

*Primary Examiner*—Johann Richter
*Assistant Examiner*—Sharon Howard
*Attorney, Agent, or Firm*—Ohlandt, Greeley, Ruggiero & Perle

[57] ABSTRACT

This cosmetic composition for treating nails includes from about 0.01 weight percent to about 10.0 weight percent stabilized hydrogen peroxide, a pH adjusting agent in an amount sufficient to maintain the cosmetic composition at a pH of from about 6 to about 9, a buffer, and water.

29 Claims, No Drawings

NAIL BLEACH

This is a continuation-in-part of copending U.S. patent application Ser. No. 08/797,992, filed Feb. 12, 1997.

The present invention relates generally to a composition for bleaching stained fingernails. More particularly, this invention relates to a pH buffered cosmetic composition containing a stabilized hydrogen peroxide that can be applied to stained fingernails to remove yellowing and stains.

BACKGROUND OF THE INVENTION

The cosmetic appearance of fingernails has long been a matter of concern to consumers. Nail polishes and artificial fingernails are among the popular cosmetic treatments applied to the nails (fingernails or toenails, hereinafter collectively called "nails"). However, regular or even occasional use of such products can leave the natural nail yellowed and stained. In addition, coffee, cigarettes, certain medications, and the use of harsh chemicals in the home, may also leave the nail undesirably yellow and uneven in color.

Products are available on the market that coat the nail with a slight purple tint, in the manner of a nail polish, to counteract the yellow coloring of the nail. However, just like nail polish, these products have limited durability, require frequent reapplication, and function only to mask the nail problem, not to correct it. Such products also do not improve the condition of the cuticle.

In addition, home bleaching remedies are also known. These remedies use oxidizing agents, such as hydrogen peroxide, in one of two types of compositions. The first of these is a stable acidic composition, in which the bleaching effectiveness of the hydrogen peroxide is curtailed. In a lower pH solution, the oxidizing activity of the hydrogen peroxide is reduced. Also, the composition does not "wet out" or disperse as effectively on the nail, limiting contact between the hydrogen peroxide and the stain. Alternatively, higher pH compositions are known. However, lower pH compositions typically require the addition of an activator. This activator must be added immediately prior to use, thus necessitating a two-phase composition.

Accordingly, a need exists for a single phase, shelf-stable nail bleaching product that effectively bleaches and removes nail stains and yellowing.

SUMMARY OF THE INVENTION

Against the foregoing background, it is a primary object of the present invention to provide a shelf-stable nail cosmetic composition for removing nail stains and yellowing.

It is another object of the present invention to provide a nail bleach composition that is premixed and does not require additional preparation by the user prior to application.

It is still another object of the present invention to provide a cosmetic composition that softens and removes dead cuticle skin.

It is a further object of the present invention to provide such a cosmetic composition that is not harmful to the nail or to healthy cuticle tissue.

It is a still further object of the present invention to provide such a cosmetic composition that is buffered against change in pH over time, to enhance stability and long-term effectiveness.

To the accomplishment of the foregoing objects and advantages, the present invention, in brief summary, comprises a nail bleach containing stabilized hydrogen peroxide in an acceptable carrier. The carrier includes a buffer component. More preferably, the nail bleach also includes a pH adjusting agent to bring the composition to a higher pH. A preferred cosmetic composition for treating nails includes from about 0.01 percent by weight or weight percent to about 10 weight percent stabilized hydrogen peroxide, a pH adjusting agent in an amount sufficient to maintain said cosmetic composition at a pH from about 8.0 to about 8.5, a buffer and water.

DESCRIPTION OF THE PREFERRED EMBODIMENTS

The present invention provides nail bleach composition or compositions that are premixed, shelf-stable and safe to the nails and healthy cuticle skin. In addition, regular use of the claimed compositions soften and remove dead cuticle skin, further improving the appearance of the nails. As discussed herein, shelf-stable cosmetic compositions are those in which the oxidizing agent does not degrade over normal product distribution periods, storage periods and temperature extremes to the point that it is no longer active.

The preferred stable nail bleach compositions of the present invention include stabilized hydrogen peroxide, in a pH buffered cosmetically acceptable carrier. The carrier preferably is water. More preferably, the carrier is demineralized water.

These compositions are not multi-component systems, but include only a single preformulated component. They require no mixing or activation immediately prior to use. These compositions can be packaged in a standard jar or other dispenser and can be applied directly to the nail and cuticle. Preferably, one composition is used on a regular basis, such as once daily, until results are achieved. If the nails are continually being stained, due to daily smoking, for example, the composition can be applied to the nails indefinitely over time. In addition, the composition can be safely applied to the nails more than once a day to accelerate the bleaching process.

The preferred stabilized hydrogen peroxide of the present invention is hydrogen peroxide in a stabilized form. A stabilized form is a form in which contact with aqueous carriers and extended storage do not result in any significant deactivation, namely chemical decomposition, of the hydrogen peroxide. The stabilized hydrogen peroxide functions as the bleaching agent in the nail bleach compositions of the present invention. At very low levels, the hydrogen peroxide will have little visible effect on nail stains. At high levels, the hydrogen peroxide will be irritating or harmful to the nail and surrounding skin. Accordingly, the stabilized hydrogen peroxide is preferably present at about 0.01 to about 10 weight percent of the composition. More preferably, the stabilized hydrogen peroxide is present at about 2 to about 5 weight percent of the composition. Most preferably, the stabilized hydrogen peroxide is present at about 3.0 to about 3.5 weight percent.

There has been found that certain stablized hydrogen peroxides work and it is believed that all stablized hydrogen peroxides will work. The preferred stablized hydrogen peroxides include stablized hydrogen peroxides sold by Solvay Intervox under the tradenames Cosmetic Grade, PeroxClean and Ultra Cosmetic. The latter two are more preferred, and the latter one is most preferred.

The PeroxClean hydrogen peroxide is preferably 35% active, and has the following properties:

|  | 35% |
|---|---|
| Typical Analysis | |
| Concentration in water, % W/W | 35.0–36.0 |
| Gasometric Stability @ 100° C., ml O$_2$/min/25 mL H$_2$O$_2$ | <0.3 |
| Active Oxygen, % w/w | 16.5 |
| Apparent pH | 2.3–2.7 |
| Typical Properties | |
| Specific Gravity, @ 20° C., g/ml | 1.13 |
| Density, lb/gal | 9.4 |
| Freezing Point °C. | −33 |
| °F. | −27 |
| Boiling Point °C. | 108 |
| °F. | 226 |

This preferred stabilized hydrogen is an alkaline stabilized hydrogen peroxide.

The Ultra Cosmetic Hydrogen Peroxide is also preferably 35% active. It has the following properties:

|  | 35% |
|---|---|
| Typical Analysis | |
| Concentration in water, % w/w | 35.0–36.0 |
| Active Oxygen, % | 16.5–17.0 |
| Gasometric Stability @ 100° C., mL O$_2$/min per 25 mL H$_2$O$_2$ | <0.3 |
| Apparent pH | 2.1–3.1 |
| Typical Properties | |
| Specific Gravity @ 20° C., g/ml | 1.13 |
| Density, lb/gal | 9.4 |
| Freezing Point °C. | −33 |
| °F. | −27 |
| Boiling Point °C. | 108 |
| °F. | 226 |

Again, this preferred stabilized hydrogen peroxide is an alkaline stabilized hydrogen peroxide. This Ultra Cosmetic Hydrogen Peroxide is 35 to 36% hydrogen peroxide, less than 2% potassium stannate, less than 2% tetrapotassium pyrophosphate, less than 2% phosphoric acid, and the balance water.

Other stablized hydrogen peroxides that can be used in the present invention include in situ stabilized hydrogen peroxide.

For the purposes of the present invention, such a stabilized hydrogen peroxide is distinguished from hydrogen peroxide-containing compositions that are stabilized only due to their low pH. In addition to the preferred stabilized hydrogen peroxide discussed above, a conventional hydrogen peroxide can also be used provided it is in combination with a stabilizer that is formulated into the composition. This combination generates a stabilized hydrogen peroxide that is within the purview of the present invention. Such stablizers include, for example, phosphoric acid; sodium pyrophosphate; sodium stannate trihydrate; stannate, phosphate, nitrate, magnesium or silicate ions; or amine-substituted organophosponic acids or their alkali metal salts.

The preferred nail bleach of the present invention includes a pH adjusting agent. The pH adjusting agent or pH adjuster is preferably sodium hydroxide. The pH adjusting agent preferably places the pH of the composition at about 6 to about 9. More preferably, the pH adjusting agent places the composition at a basic pH (greater than 7), and most preferably at a pH about 8.0 to about 8.5. It is believed that this preferred slight alkalinity of the nail bleach is the primary source of its ability to effectively soften cuticles. The pH adjusting agent also acts to accelerate the bleaching process. The pH adjusting component concentration, as well as water level, can be adjusted to achieve this desired pH range.

Any cosmetically acceptable pH adjusting agent or agents can be used in the compositions of the present invention, provided they do not deactivate the peroxide or contain contaminants. The preferred pH adjusting agents are sodium hydroxide and ammonium hydroxide. Sodium hydroxide is the more preferred pH adjusting agent. Other useful pH adjusting agents include caustic soda and other hydroxides, carbonates, silicates, pyrophosphates, polyphosphates and amines. When sodium hydroxide is the pH adjusting agent, the most preferred pH in the range of about 8.0 to about 8.5 is achieved.

The nail bleach of the present invention may include a buffer to further stabilize the pH of the composition. By further stabilization, it is meant that the buffer will enhance or increase the shelf-life of the nail bleach product. The buffer may be used separate from or in addition to a pH adjusting agent in order to maintain the pH of the composition over time, preferably in the range of about 6 to about 9. As discussed above, the composition is more preferably maintained at a basic pH (greater than 7), and most preferably at a pH about 8.0 to about 8.5.

Any cosmetically acceptable buffer or combination of buffers can be used in the compositions of the present invention, provided they do not contain contaminants at a level sufficient to decompose the hydrogen peroxide.

The buffer is preferably present at about 0.1 weight percent to about 2 weight percent of the composition. The preferred buffer for use in the nail bleach compositions of the present invention is anhydrous disodium phosphate. When anhydrous disodium phosphate is used as the buffer, it is most preferably present at about 1 weight percent. Anhydrous disodium phosphate is preferred for use in the nail bleach compositions of the present invention because: 1) it is readily available at a pharmaceutical/food grade thus ensuring that it contains little or no contaminants; 2) the potential for irritation is minimized; 3) one of its pKa values is appropriate for the preferred pH range of the compositions; 4) its solubility profile is compatible with the preferred batch ingredients to minimize cloudiness; and 5) it is a sodium salt, which provides common ion compatibility. Other useful buffers include, but are not limited to, sodium benzoate, sodium borate, dibasic sodium phosphate, dibasic potassium phosphate, potassium citrate, sodium citrate, tetrapotassium pyrophosphate and tetrasodium pyrophosphate.

To provide a cosmetically pleasing product and to aid in delivering the stabilized hydrogen peroxide to the nail and cuticle area, a thickener (or thickeners) is preferably added to the nail bleach composition of the present invention. Any cosmetic thickener suitable for use with an aqueous peroxide composition may be used in the present composition. The thickener is preferably present at a range about 0.1 to about 20 weight percent. More preferably, the thickener is present in a range of about 1 to about 5 weight percent. Thickeners, such as acrylic acid polymers (e.g. Carbopol), steareth-10 alkyl ether/acrylate copolymer (preferably Salcare SC90 sold by Allied Colloids Inc., an associative thickener), and a polyoxypropylene/polyoxyethylene block copolymer (which also acts as an anti-irritant) are preferred, alone or in combination. Steareth-10 alkyl ether/acrylate copolymer and the polyoxypropylene/polyoxyethylene block copolymer are most preferred. The most preferred polyoxypropylene/polyoxyethylene block copolymer is Pluoronic F127 (POE(196M)-POP(67M) block polymer) by BASF Corporation.

One or more surfactants can also function in compositions of the present invention to reduce the surface tension of the composition, to enhance "wet out" or dispersion of the hydrogen peroxide on the nail. Degreasing or cleansing surfactants that are compatible with peroxides are preferred for use in the compositions of the present invention. The most preferred such surfactant is lauryl sulfate.

Additional ingredients, such as vitamins, glycerin, healing agents and treatment agents, fragrances may also be added to the nail bleach composition.

Panthenol is a preferred vitamin for use in the present invention. It is preferably present at about 0.01 weight percent.

Glycerin acts to moisturize the nails and cuticles. Glycerin is preferably present at up to about 2 weight percent. More preferably, glycerin is present at about 0.5 weight percent.

The healing agents may include, for example, green tea extract or aloe or a combination thereof. The treatment agents may include, for example, aldehyde.

A fragrance may be added to the nail bleach composition to enhance its appeal and acceptability. The fragrance is preferably present at up to about 5 weight percent. The fragrance is most preferably present in a range about 0.0001 to about 1.0 weight percent. Any compatible cosmetic fragrance may be used. Compatible means that the fragrance works with the system without any deleterious effects.

Certain active ingredients, such as stabilized hydrogen peroxide, the pH adjusting agent, such as sodium hydroxide, are provided in solution containing a percentage of active ingredients. For example, the hydrogen peroxide solution of the foregoing preferred embodiment is present at 9.71 weight percent of 35% active solution. Accordingly, stabilized hydrogen peroxide, as the term is used in the appended claims, is present at about 3.4 weight percent (0.35×0.0971= 0.034).

The following are preferred exemplary nail bleach compositions having a buffer according to the present invention:

EXAMPLE 1

NAIL BLEACH

|  | Wt. % |
| --- | --- |
| Demineralized water | 80.74 |
| Hydrogen peroxide 35% - alkaline stabilized | 9.71 |
| Sodium hydroxide solution 50% | 0.44 |
| Disodium phosphate-anhydrous | 1.00 |
| Polyoxypropylene/polyoxyethylene block polymer | 5.00 |
| Steareth-10 alkyl ether/ acrylate copolymer | 2.50 |
| Glycerin | 0.50 |
| Panthenol | 0.01 |
| Fragrance | 0.10 |

EXAMPLE 2

NAIL BLEACH

|  | Wt. % |
| --- | --- |
| Deionized water | 81.42 |
| Ultra cosmetic peroxide (35% active) | 9.71 |
| Sodium hydroxide (25% active) | 0.77 |
| Disodium phosphate-anhydrous | 1.00 |
| Steareth-10 alkyl ether/ acrylate copolymer | 2.00 |
| Polyoxypropylene/polyoxyethylene block copolymer | 5.00 |
| Fragrance | 0.1 |

While the improved cosmetic appearance of fingernails is a primary object of the present invention, it is evident that stained or yellowed toenails, for example, can also be treated by the claimed compositions and methods. Toenails are also commonly coated with nail polish, and can also be stained by such things as medications or dyes in socks or other footwear.

The present invention having been thus described with particular reference to the preferred forms thereof, it will be obvious that various changes and modifications may be made therein without departing from the spirit and scope of the invention as defined in the appended claims.

What we claim is:

1. A shelf-stable, single phase nail bleach composition comprising:

from about 0.01 weight percent to about 10 weight percent alkaline-stable hydrogen peroxide;

from about 0.1 weight percent to about 2 weight percent buffer; and a cosmetically acceptable carrier.

2. The nail bleach composition of claim 1, wherein said hydrogen peroxide is present at about 2 weight percent to about 5 weight percent.

3. The nail bleach composition of claim 1, further comprising a pH adjusting agent.

4. The nail bleach composition of claim 3, wherein said pH adjusting agent is sodium hydroxide.

5. The nail bleach composition of claim 4, wherein said sodium hydroxide is present at about 0.8 weight percent.

6. The nail bleach composition of claim 3, wherein said nail bleach composition has a basic pH.

7. The nail bleach composition of claim 6, wherein said pH is from about 8.0 to about 8.5.

8. The nail bleach composition of claim 1, further comprising a thickener.

9. The nail bleach composition of claim 8, wherein said thickener is present from about 0.1 to about 20 weight percent.

10. The nail bleach composition of claim 9, wherein said thickener is present from about 1 to about 5 weight percent.

11. The nail bleach of claim 8, wherein said thickener is copolymeric.

12. The nail bleach of claim 11, wherein said thickener is a steareth-10 alkyl ether/acrylate copolymer.

13. The nail bleach of claim 1, further comprising a surfactant.

14. The nail bleach of claim 13, wherein said surfactant is a degreasing surfactant.

15. The nail bleach of claim 14, wherein said surfactant is a lauryl sulfate.

16. The nail bleach of claim 13, wherein said surfactant is a cleansing surfactant.

17. The nail bleach of claim 1, wherein said buffer includes disodium phosphate.

18. The nail bleach of claim 17, wherein said disodium phosphate is anhydrous.

19. The nail bleach of claim 17, wherein said buffer is present at about 1 weight percent.

20. A shelf-stable, single phase nail bleach composition comprising:

from about 0.01 weight percent to about 10 weight percent alkaline-stable hydrogen peroxide in combination with a stabilizer; and a cosmetically acceptable carrier.

21. A cosmetic composition for treating nails, comprising:

from about 0.01 weight percent to about 10 weight percent stabilized hydrogen peroxide;

a pH adjusting agent in an amount sufficient to maintain said cosmetic composition at a pH from about 8.0 to about 8.5;

a buffer in an amount sufficient to keep said pH stable; and water.

22. The cosmetic composition of claim 21, further comprising a thickener.

23. The cosmetic composition of claim 21, wherein said pH adjusting agent is sodium hydroxide.

24. The cosmetic composition of claim 23, wherein said sodium hydroxide is present at about 0.8 weight percent.

25. The cosmetic composition of claim 22, wherein said thickener is copolymeric.

26. The cosmetic composition of claim 25, wherein said thickener is a steareth-10 alkyl ether/acrylate copolymer.

27. The cosmetic composition of claim 21, wherein said buffer includes disodium phosphate.

28. A method of removing stains from nails, comprising:

applying to the nails a shelf-stable nail bleach composition comprising:

from about 0.01 weight percent to about 10 weight percent stabilized hydrogen peroxide;

from about 0.1 weight percent to about 2 weight percent buffer; and a cosmetically acceptable carrier.

29. A method of improving cuticles, comprising:

applying to the cuticles a shelf-stable nail bleach composition comprising:

from about 0.01 weight percent to about 10 weight percent stabilized hydrogen peroxide;

from about 0.1 weight percent to about 2 weight percent buffer; and a cosmetically acceptable carrier.

* * * * *